United States Patent [19]

Knight et al.

[11] 4,170,043
[45] Oct. 9, 1979

[54] COATED INTRAOCULAR LENS AND SURGICAL TOOL

[75] Inventors: Patricia M. Knight, Costa Mesa; William J. Link, Irvine, both of Calif.

[73] Assignee: American Hospital Supply Corporation, Evanston, Ill.

[21] Appl. No.: 855,961

[22] Filed: Nov. 30, 1977

[51] Int. Cl.² ............... A61F 1/16; A61F 9/00; A61F 1/24; A61B 17/28
[52] U.S. Cl. ................... 3/13; 128/303 R; 128/321
[58] Field of Search ........... 3/13, 1; 128/303 R, 128/321-324

[56] References Cited

U.S. PATENT DOCUMENTS

| | | | |
|---|---|---|---|
| 3,996,626 | 12/1976 | Richards et al. | 3/13 |
| 4,047,532 | 9/1977 | Phillips et al. | 128/303 R |
| 4,113,088 | 9/1978 | Binkhorst | 3/13 X |
| 4,127,903 | 12/1978 | Schachar | 3/13 |
| 4,136,406 | 1/1979 | Norris | 3/13 |

OTHER PUBLICATIONS

"Corneal Endothelium Damage with Intraocular Lenses: Contact Adhesion Between Surgical Materials and Tissue," by H. E. Kaufman et al., Science, vol. 198, (4316), Nov. 4, 1977, pp. 525-527.
"Endothelial Damage from Intraocular Lens Insertion," by H. E. Kaufman et al., Investigative Ophthalmology, vol. 15, (12), Dec. 1976, pp. 996-1000.
"Prevention of Endothelial Damage from Intraocular Lens Insertion," by H. E. Kaufman et al., Tr. Am. Acad. Ophthalmology & Otol., vol. 83, Mar.-Apr. 1977, pp. 204-212.
"Pathology of the Corneal Endothelium," Investigative Ophthalmology, vol. 16, (4), Apr. 1977, pp. 265-268.
"Methylcellulose in Lens Implantation," Journal Amer. Intraocular Implant Society, vol. 3, (3&4), Jul.-Oct. 1977, pp. 180-181, by P. U. Fechner.

Primary Examiner—Ronald L. Frinks
Attorney, Agent, or Firm—Larry N. Barger

[57] ABSTRACT

An intraocular lens or surgical tool used for eye surgery which is covered with a biocompatible water-soluble adherent film coating that has a very slow dissolution rate which maintains at least 40% of the coating on the lens for at least 30 minutes, but not more than 24 hours, when submerged in an aqueous media simulating the surgical environment. Polyvinyl alcohol is an example of such coating that is dissolvable in water and provides swellable outer portions of the coating that are sluffable so as to be self-sacrificing in protecting against both static and sliding contact with a corneal endothelium.

42 Claims, 5 Drawing Figures

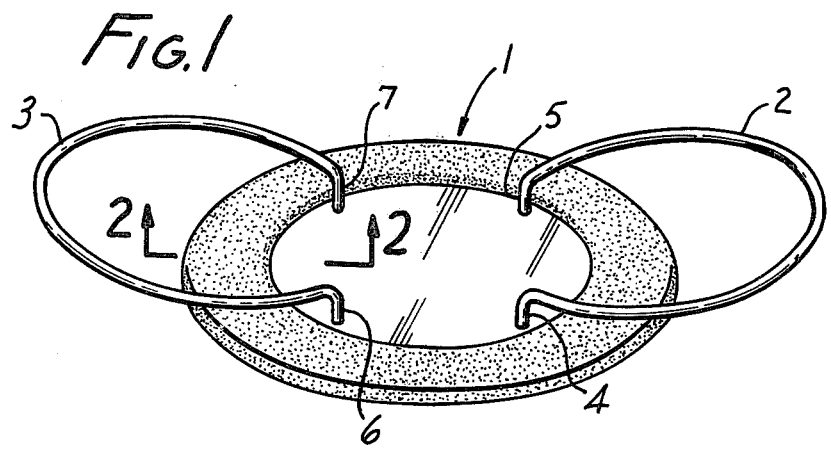
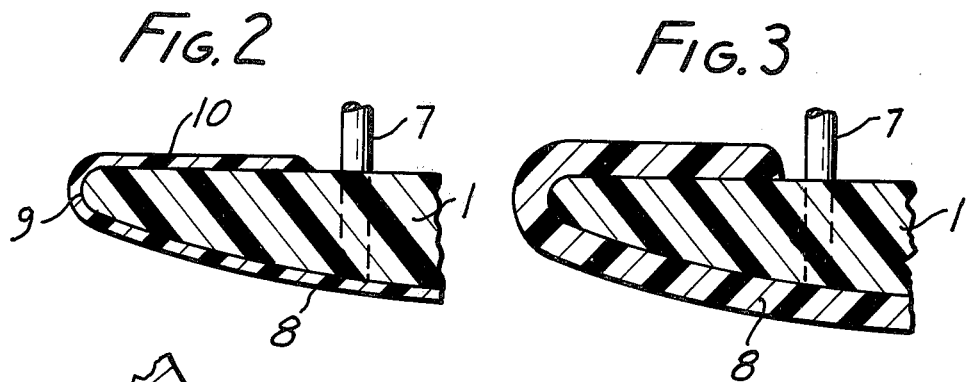
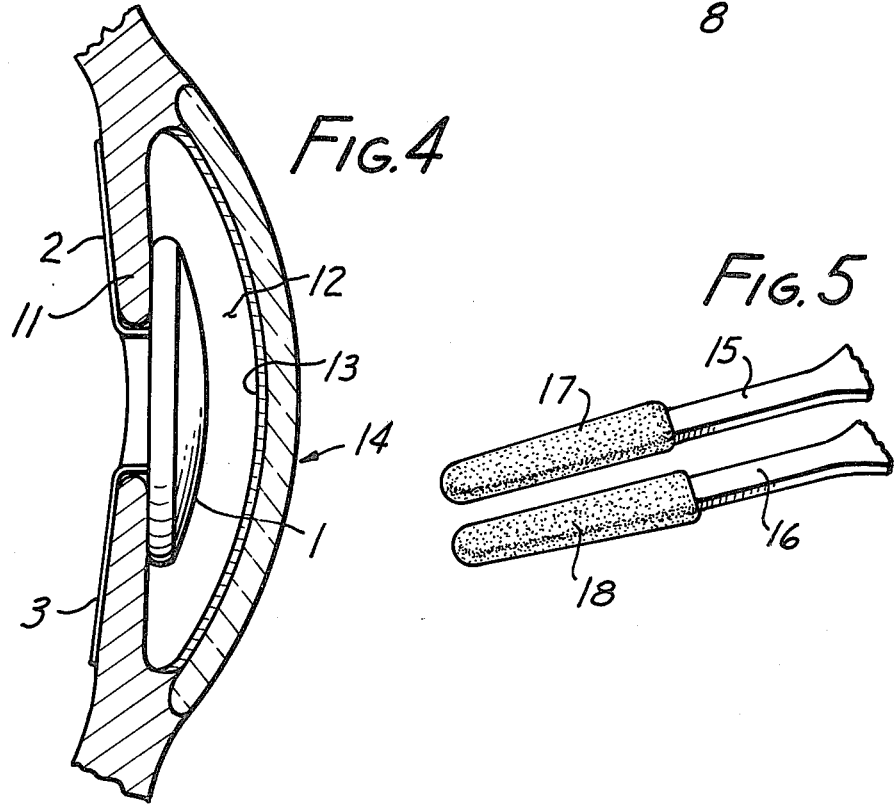

COATED INTRAOCULAR LENS AND SURGICAL TOOL

BACKGROUND

When the natural lens of the human eye becomes physically damaged or has some disease necessitating its removal, such as a cataract, it is often replaced with an artificial intraocular lens.

During the process of surgically implanting such lens through an incision at the edge of the cornea, it has been found that static touching of the corneal endothelium with a polymethylmethacrylate (PMMA) or other surgical tool, can permanently destroy a portion of the endothelial cells. It is generally recognized that the human endothelium, which is only one cell layer thick, cannot regenerate itself by producing additional cells. It appears that more damage is done to the corneal endothelium by a dynamic or sliding contact with such lens or tool during surgery as compared to a static or nonsliding contact with the endothelium. The corneal endothelium is very critical to the eye as it is a barrier between the outer layers of the cornea and the aqueous humor in the anterior chamber. After surgery, the location of the intraocular lens is such that, when in its proper position, it does not contact or damage the corneal endothelium.

It has been suggested by others to coat the intraocular lens with methylcellulose (MC) or polyvinylpyrrolidone (PVP). The following publications describe such coating.

Kaufman, H. E. and J. I. Katz, "Endothelial Damage From Intraocular Lens Insertion," *Inv. Ophth.*, Vol. 15(12), December 1976, p. 996–1000

Kaufman, H. E., Jeffrey Katz, et al, "Prevention of Endothelial Damage From Intraocular Lens Insertion," *Tr. Am. Acad. Ophth. & Otol.*, Vol. 83, March-April 1977, p. 204–212

Kaufman, H. E. and J. I. Katz, "Pathology of the Corneal Endothelium," *Inv. Ophth. Visual Sci.*, Vol. 16(4), April 1977, p. 265–268

Fechner, P. U., "Methylcellulose in Lens Implantation," *Jour. Amer. Intraocular Implant Society*, Vol. 3(3 & 4), July-October 1977, p. 180–181

Kaufman, H. E., Jeffrey Katz, et al, "Corneal Endothelium Damage with Intraocular Lenses: Contact Adhesion Between Surgical Materials and Tissue," *Science*, Vol. 198(4316), November, 4, 1977, p. 525–527.

While the above coatings of MC and PVP helped protect the corneal endothelium during surgery, they had several shortcomings. A supply of methylcellulose used by Dr. Kaufman in the above publications was obtained from him and tested. It was found to be a very poor film former and tended to "bead up" on the PMMA lens exposing edges of the lens. It has been found that MC has a very fast dissolution rate. Dipping of lenses in MC or PVP is useful to protect the corneal endothelium. However, because of the fast dissolution rate of these polymers and the difficulty of placing a controlled amount of such polymers on the lenses, the extent and length of time of protection is uncontrollable. Because of the wet and slippery nature of lenses dipped during surgery, the lenses are difficult to handle and a portion of the coating may drip off. In addition, MC and PVP solutions must be sterilized prior to dipping. The amount and type of contact with the corneal endothelium varies with the skills and techniques of different ophthalmic surgeons. It is highly desirable to have a coating that protects against both static and dynamic sliding contact.

SUMMARY OF THE INVENTION

The present invention overcomes the above problems by providing an adherent film coating that dissolves very slowly in water. This coating is on an intraocular lens or ophthalmic surgery tool and is supplied in a dehydrated state to the ophthalmologist who rehydrates the coating immediately prior to surgery. This coating, such as polyvinyl alcohol, clings to the lens or the like and maintains at least 40% of the coating on the lens for at least 30 minutes when submerged in a water bath simulating the wet surgical site. The coating is biocompatible and dissolvable in approximately 24 hours or less after surgery so as not to remain on the lens.

The present application deals with the coated intraocular lens and surgical tools themselves. A related co-pending application by the same inventors entitled "Method of Treating Intraocular Lens Or The Like," filed Nov. 30, 1977, Ser. No. 855,962, deals with the method of coating, dehydrating, and rehydrating a lens or surgical tool.

THE DRAWINGS

FIG. 1 is a rear prospective view of an intraocular lens coated according to this invention;

FIG. 2 is an enlarged sectional view taken along line 2—2 of FIG. 1 showing the coating in a dehydrated state;

FIG. 3 is an enlarged sectional view similar to that of FIG. 2, but showing the coating in a hydrated state;

FIG. 4 is a sectional view schematically showing the intraocular lens implanted within an eye; and FIG. 5 is a fragmentary prospective view of coated tip sections of an ophthalmic surgery forceps.

DETAILED DESCRIPTION

FIG. 1 shows the rear of a typical intraocular lens with an optic section indicated generally as 1. To this optic section are secured a pair of iris engaging retention loops 2 and 3 that include shank sections, such as 4, 5, 6, and 7 securing the loops to the optic portion of the lens.

A lens coating shown as 8 covers the entire front surface of the optical portion 1 of the lens. It is the front surface of this lens that is most likely to contact the corneal endothelium during surgery. The coating covers a peripheral edge of the lens, as at 9, and can also include a circumferential band 10 on a back surface of the optical section 1, if desired. Thus, all portions of the intraocular lens that are likely to contact the corneal endothelium are adequately protected. The iris retention loops are not coated, because the coating bridges the loops and accumulates excessive material on the loops. It is desirable to keep the coating material to a minimum amount so it does not biologically interfere with the function of the eye and can readily be absorbed by the body. It is believed that such coating of this invention is removed from the eye through the continuous biological flushing of the anterior chamber. The dissolved material is eventually excreted through the urine or metabolized.

FIG. 2 shows the coating after it has been applied and dehydrated to remove substantially all of the water in the coating during the application step. The lens with the dehydrated coating is encased in a microbial barrier package and then sterilized. Thus, the sterile precoated lens with its dehydrated protective layer can be stored and shipped to the ophthalmologist. Because many different types of packages could be used, it is not believed necessary to schematically illustrate a package nor to illustrate the sterilizing equipment.

In FIG. 3, the dehydrated coating 8 has been submerged in an aqueous medium, such as a balanced salt solution. After a few minutes in the aqueous media, the dehydrated coating rehydrates and swells to a thickness at least ⅓ greater than its dehydrated thickness. This swollen coating has a property of sluffing off outer portions of the coating during sliding contact with the corneal endothelium. It also protects the endothelium from contact with the lens' optical section 1 during static touch contact to the endothelium.

The sectional view of FIG. 4 shows a schematic of a human eye with the optical section 1 implanted and retained by loops 2 and 3 which are secured behind the iris 11. In FIG. 4, the optical section 1 is shown in the eye's anterior chamber. It is understood that this invention could be used on anterior chamber lenses, posterior chamber lenses, and lenses that use retention means other than iris loops.

Once the intraocular lens is implanted, aqueous humor within the anterior chamber 12 protects the corneal endothelium layer 13 and provides a cushion between such endothelium and the optical element of the lens. The cornea, which includes the endothelium, is shown generally at 14. In FIG. 4, the coating 8 has been completely dissolved off optical element 1 after implantation. It is estimated that this dissolution takes place within about 2-24 hours.

In addition to an intraocular lens, the coating can be applied to ophthalmic surgery tools, such as the tip sections 15 and 16 of a forceps. A typical forceps might be a Von Graefe iris forceps. In FIG. 5, the coating on such forceps is shown at 17 and 18.

The coating described above has a dissolution rate sufficiently slow so that at least 40% of the coating remains on the lens or the surgical tool for at least 30 minutes when submerged in a water bath simulating the surgical environment. During surgery, the lens is at approximately room temperature, although at times it might be slightly higher, i.e. at body temperature. This slight temperature change is believed to be insignificant much of the time during surgery the lens and tools are exposed to air temperature.

After the coating is applied to the lens or the like, it is dehydrated until it is substantially dry and has a thickness of from 5 to 300 microns. Very successful results have been obtained with coating of approximately 100 microns thick. Plural coatings can be applied to build up this thickness. Once rehydrated by the ophthalmic surgeon, the coating swells to a thickness of from 10 to 1000 microns. The hydrated coating is preferably at least ⅓ thicker than the dehydrated coating.

TEST PROCEDURE

A test was performed to determine the dissolution time of various water-soluble polymers coated on a PMMA intraocular lens as a function of time in a volume of liquid approximating that of the anterior chamber. Percent of weight loss of the coating as a function of time in the volume of water was calculated. The procedure involved placing a coated lens into a volume of approximately 0.2 ml distilled water. After a specified time, the lens was removed and placed on a filter pad and dehydrated for 2 hours and weighed. Weight loss was calculated and the procedure repeated until the coating had completely dissolved. The water bath was replaced with clean water after 1 hour of accumulative soak time to simulate the biological flushing action of the eye. The representative cumulative weight loss percents were plotted against cumulative time in the water bath. The following are the test results.

| Material | Thickness | No. of Coats | % Coating Remaining After 30 Minutes |
|---|---|---|---|
| PVP | 156 μ | 2 | 25% |
| PVA | 108 μ | 3 | 75% |
| HPC | 122 μ | 4 | 50% |
| HPMC | 98 μ | 4 | 50% |
| Dextran | 200 μ | 1 | 0% |
| HES | 236 μ | 1 | 0% |
| MC | Poor film former; beaded up to expose edges of lens; and dissolved very quickly. | | |

In the above tests, the abbreviations are as follows:
HPMC (hydroxypropyl methylcellulose); HPC (hydroxypropyl cellulose); HES (hydroxyethyl starch).

In the above tests, the abbreviations are as follows:
HPMC (hydroxypropyl methylcellulose); HPC (hydroxypropyl cellulose); HES (hydroxyethyl starch).

Because methylcellulose as tested by Dr. Kaufman and other would not stick to the lens, it was disregarded as a proper coating. It may be possible to blend methylcellulose with other adherent film formers or to specially treat the lens to get better adherents to approximate the coating film described in the present invention. It has been shown unaltered methylcellulose applied to an unaltered PMMA lens as in the work by Dr. Kaufman and others is a poor lens coating for the reasons specified above.

While the most successful tests to date have been made with polyvinyl alcohol, other water-soluble and swellable polymers meeting the above criteria of the applicants could be used. Possible other polymers are hydroxypropyl methylcellulose, hydroxypropyl cellulose, and Jaguars. Jaguar is a trade name of Stein-Hall Specialty Chemicals for their guar gum and guar drivatives. It is also possible to use mixtures of materials to form a coating that is both (1) an adherent film former and (2) has a slow dissolution rate to maintain at least 40% of the coating on the lens or the like for at least 30 minutes according to this invention.

During portions of the surgery, the coated intraocular lens or surgical tool is not in the wet surgical site, but is exposed to air. It is important that the coating in its swollen hydrated state does not quickly dehydrate when subjected to air. It has been found that the polyvinyl alcohol coating will maintain its swollen hydrated state for at least 20 minutes when exposed to ambient air.

The intraocular lens or surgical tools can be conveniently coated by dipping into a 5% aqueous solution of polyvinyl alcohol. Preferably, two dip coats are applied allowing the lens or tool to air dry between dips.

In the above description, a specific example has been used to illustrate the invention. However, it is understood by those skilled in the art that certain modifications can be made to this example without departing from the spirit and scope of the invention.

We claim:

1. An intraocular lens having a surface likely to contact a corneal endothelium during ophthalmic surgery, wherein the improvement comprises: a biocompatible water-soluble adherent film coating on such surface for protecting the corneal endothelium, said coating having a dissolution rate sufficiently slow so that at least 40% of the coating is maintained on the device for at least 30 minutes when submerged in an aqueous media at room temperature that has a volume simulating that of the aqueous humor.

2. The lens as set forth in claim 1, wherein the aqueous media is approximately 0.2 ml of water.

3. The lens as set forth in claim 2, wherein the coating is capable of maintaining such loss rate when the approximately 0.2 ml of water is changed every hour to simulate the continuous flow of aqueous humor in the eye.

4. The lens as set forth in claim 1, wherein the coating is dissolvable in the aqueous media and clearable from the eye.

5. The lens as set forth in claim 1, wherein the coating is in a dehydrated state prior to submersion, and the coating is water swellable in a time period that is less than required for completely dissolving.

6. The lens device as set forth in claim 1, wherein the coating is in a swollen hydrated state and has outer portions of the coating that are sluffable during sliding and nonsliding contact with a corneal endothelium.

7. The lens as set forth in claim 1, wherein the coating is in a swollen hydrated state and the coating is dissolvable to expose at least a portion of the surface area beneath the coating in a time period more than 30 minutes but less than 24 hours when submerged in an aqueous media at room temperature simulating an implanted lens.

8. The lens as set forth in claim 1, wherein the coating is in a swollen hydrated state and is capable of maintaining said hydrated state without substantial dehydration for a period of at least 20 minutes when exposed to ambient air.

9. The lens as set forth in claim 1, wherein the coating is in a dehydrated state for storage and shipping.

10. The lens as set forth in claim 1, wherein the coating is a water swellable polymer.

11. The lens as set forth in claim 10, wherein the coating is polyvinyl alcohol.

12. The lens as set forth in claim 1, wherein the coating includes a plurality of applied coating layers.

13. The lens as set forth in claim 1, wherein the coating in its dehydrated state has a thickness of from 5 to 300 microns.

14. The lens as set forth in claim 1, wherein the coating in its hydrated state has a thickness of from 10 to 1000 microns.

15. The lens as set forth in claim 1, wherein only a portion of the lens is coated.

16. A intraocular lens comprising: an optical section; and a polyvinyl alcohol coating covering at least a portion of the optical section.

17. A lens as set forth in claim 16, wherein the polyvinyl alcohol is in a dehydrated state.

18. A lens as set forth in claim 17, wherein the coating is rehydratable to provide outer portions of the coating that are sluffable to reduce damage to a corneal endothelium during sliding and nonsliding contact with such endothelium.

19. A lens as set forth in claim 16, wherein the optical section is polymethylmethacrylate.

20. A lens as set forth in claim 17, wherein the precoated intraocular lens with its dehydrated coating are sterile and within a sterility maintaining package.

21. An intraocular lens having a surface likely to contact a corneal endothelium during ophthalmic surgery, wherein the improvement comprises: a biocompatible water-soluble adherent film coating on such surface for protecting a corneal endothelium, said coating having a dissolution rate sufficiently slow so that at least 40% of the coating is maintained on the device for at least 30 minutes when submerged in an aqueous media at room temperature that has a volume simulating that of the aqueous humor, said coating having portions that are sluffable during sliding and nonsliding contact with a corneal endothelium.

22. A surgical tool having a surface likely to contact a corneal endothelium during ophthalmic surgery wherein the improvement comprises: a biocompatible water-soluble adherent film coating on such surface having a dissolution rate sufficiently slow so that at least 40% of the coating is maintained on the device for at least 30 minutes when submerged in an aqueous media at room temperature that has a volume simulating that of the aqueous humor.

23. The tool as set forth in claim 22, wherein the aqueous media is approximately 0.2 ml of water.

24. The tool as set forth in claim 23, wherein the coating is capable of maintaining such loss rate when the approximately 0.2 ml of water is changed every hour to simulate time continuous flow of aqueous humor in the eye.

25. The tool as set forth in claim 22, wherein the coating is dissolvable in the aqueous media and clearable from the eye.

26. The tool as set forth in claim 22, wherein the coating is in a dehydrated state prior to submersion, and the coating is water swellable in a time period that is less than required for completely dissolving.

27. The tool as set forth in claim 22, wherein the coating is in a swollen hydrated state and has outer portions of the coating that are sluffable during sliding and nonsliding contact with a corneal endothelium.

28. The tool as set forth in claim 22, wherein the coating is in a swollen hydrated state and the coating is dissolvable to expose at least a portion of the surface area beneath the coating in a time period more than 30 minutes but less than 24 hours when submerged in an aqueous media at room temperature simulating conditions of an eye.

29. The tool as set forth in claim 22, wherein the coating is in a swollen hydrated state and is capable of maintaining said hydrated state without substantial dehydration for a period of at least 20 minutes when exposed to ambient air.

30. The tool as set forth in claim 22, wherein the coating is in a dehydrated state for storage and shipping.

31. The tool as set forth in claim 22, wherein the coating is a water swellable polymer.

32. The tool as set forth in claim 31, wherein the coating is polyvinyl alcohol.

33. The tool as set forth in claim 22, wherein the coating includes a plurality of applied coating layers.

34. The tool as set forth in claim 22, wherein the coating in its dehydrated state has a thickness of from 5 to 300 microns.

35. The tool set forth in claim 22, wherein the coating in its hydrated state has a thickness of from 10 to 1000 microns.

36. The tool as set forth in claim 22, wherein only a portion of the tool is coated.

37. A surgical tool comprising: a section adapted to be inserted into an eye adjacent a corneal endothelium; and a polyvinyl alcohol coating covering at least a portion of this section.

38. The tool as set forth in claim 37, wherein the polyvinyl alcohol is in a dehydrated state.

39. The tool as set forth in claim 38, wherein the polyvinyl alcohol coating is rehydratable to provide outer portions of the coating that are sluffable to reduce damage to a corneal endothelium during sliding and nonsliding contact with such endothelium.

40. The tool as set forth in claim 37 wherein the tool is precoated with the polyvinyl alcohol coating being a dehydrated state, and the coated tool is sterile and within a sterility maintaining package.

41. A surgical tool having a surface likely to contact a corneal endothelium during opthalmic surgery, wherein the improvement comprises: a biocompatible water-soluble adherent film coating on such surface for protecting a corneal endothelium, said coating having a dissolution rate sufficiently slow so that at least 40% of the coating is maintained on the device for at least 30 minutes when submerged in an aqueous media at room temperature that has a volume simulating that of the aqueous humor, said coating having portions that are sluffable during sliding and nonsliding contact with a corneal endothelium.

42. A precoated opthalmic surgery tool comprising: a tip section; and a polyvinyl alcohol coating covering at least a portion of the tip.

* * * * *